US005698080A

United States Patent [19]
Berg

[11] Patent Number: 5,698,080
[45] Date of Patent: Dec. 16, 1997

[54] SEPARATION OF PHELLANDRENE FROM LIMONENE BY AZEOTROPIC DISTILLATION

[76] Inventor: Lloyd Berg, 1314 S. Third Ave., Bozeman, Mont. 59715

[21] Appl. No.: 755,407

[22] Filed: Nov. 22, 1996

[51] Int. Cl.$^6$ ................ B01D 3/36; C07C 7/06
[52] U.S. Cl. ................ 203/57; 203/59; 203/60; 203/62; 203/63; 203/66; 585/350; 585/860; 585/864; 585/866
[58] Field of Search ................ 203/57, 60, 63, 203/66, 59, 62; 585/350, 860, 864, 862, 866

[56] References Cited

U.S. PATENT DOCUMENTS

| | | | |
|---|---|---|---|
| 3,987,121 | 10/1976 | Koppel et al. | 203/64 |
| 4,136,126 | 1/1979 | Hirschy et al. | 585/355 |
| 4,508,930 | 4/1985 | Wideman et al. | 585/377 |
| 5,069,756 | 12/1991 | Berg | 203/51 |
| 5,380,405 | 1/1995 | Berg | 203/57 |
| 5,391,264 | 2/1995 | Berg | 203/57 |
| 5,582,693 | 12/1996 | Berg | 203/57 |
| 5,597,455 | 1/1997 | Berg | 203/57 |

*Primary Examiner*—Virginia Manoharan

[57] ABSTRACT

Phellandrene is difficult to separate from limonene because of the proximity of their boiling points. They are readily separated by azeotropic distillation. Effective agents are ethanol, dioxolane and acetonitrile.

1 Claim, No Drawings

SEPARATION OF PHELLANDRENE FROM LIMONENE BY AZEOTROPIC DISTILLATION

FIELD OF THE INVENTION

This invention relates to a method of separating phellandrene from limonene using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or two of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | | Theoretical Stages at Total Reflux | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 28 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

There are a number of commercial processes which produce complex mixtures of terpenes, e.g. turpentine. Two of the close boiling compounds found there are phellandrene and liminene which boil only three degrees apart. A process to separate these two would enhance their value as pure compounds. The relative volatility between these two is 1.25 which makes it difficult to separate by conventional rectification.

Azeotropic distillation would be an attractive method of effecting the separation of these two if agents can be found that (1) will create a large apparent relative volatility among these two and (2) are easy to recover from the azeotropic agent. Table 2 shows the relative volatility required to obtain 99% purity. With an agent giving a relative volatility of 1.75, only 23 actual plates are required.

TABLE 2

Theoretical and Actual Plates Required vs. Relative Volatility for Terpene Separation

| Relative Volatility | Theoretical Plates Required At Total Reflux, 99% Purity | Actual Plates Required 75% Efficiency |
|---|---|---|
| 1.4 | 28 | 38 |
| 1.6 | 20 | 27 |
| 1.75 | 17 | 23 |

OBJECTIVE OF THE INVENTION

The object of this invention is to provide a process or method of azeotropic distillation that will enhance the relative volatility of phellandrene and limonene in their separation in a rectification column. It is a further object of this invention to identify organic compounds which in addition to the above constraints, are stable, can be separated from the phellandrene or limonene and recyled to the column with little decomposition.

SUMMARY OF THE INVENTION

The objects of this invention are provided by a process for separating phellandrene from limonene which entails the use of certain organic compounds as the agent in azeotropic distillation.

DETAILED DESCRIPTION OF THE INVENTION

I have discovered that certain organic compounds will greatly improve the relative volatility between phellandrene and limonene and permit separation by rectification when employed as the agent in azeotropic distillation. Table 3 lists the compounds that I have found to be effective in separating phellandrene from limonene by azeotropic distillation. They are ethyl acetate, 2-methoxyethanol, t-butyl methyl ether, ethyl formate, methyl propionate, ethyl lactate, ethanol, isopropanol, 1-propanol, n-butanol, 2-pentanol, 2-methyl-1-propanol, t-amyl alcohol, methanol, 1-methoxy-2-propanol, acetal, 1,4-dioxane, 4-hydroxy-4-methyl-2-pentanone, dioxolane, 2-2-dimethoxypropane, dimethylformamide, butyraldehyde, ethanolamine, acetonitrile, acetone, 2-butanone, 3-pentanone, and cyclopentanone.

TABLE 3

Effective Azeotropic Distillation Phellandrene From Limonene

| Compound | Relative Volatility |
|---|---|
| None | 1.25 |
| Ethyl acetate | 1.4 |
| 2-Methoxyethanol | 1.55 |
| t-Butyl methyl ether | 1.35 |
| Ethyl formate | 1.35 |
| Methyl propionate | 1.45 |
| Ethyl lactate | 1.35 |
| Ethanol | 1.6 |
| Isopropanol | 1.35 |
| 1-Propanol | 1.4 |
| n-Butanol | 1.35 |
| 2-Pentanol | 1.45 |
| 2-Methyl-1-propanol | 1.35 |
| t-Amyl alcohol | 1.45 |
| Methanol | 1.6 |

TABLE 3-continued

Effective Azeotropic Distillation Phellandrene From Limonene

| Compound | Relative Volatility |
|---|---|
| 1-Methoxy-2-propanol | 1.45 |
| Acetal | 1.45 |
| 4-Hydroxy-4-methyl-2-pentanone | 1.35 |
| 1,4-Dioxane | 1.45 |
| Dioxolane | 1.45 |
| 2,2-Dimethoxypropane | 1.6 |
| Dimethylformamide | 1.6 |
| Butyraldehyde | 1.45 |
| Ethanolamine | 1.4 |
| Acetonitrile | 1.7 |
| Acetone | 1.5* |
| 2-Butanone | 1.45 |
| 3-Pentanone | 1.4 |
| Cyclopentanone | 1.5 |

*Reverses the volatility

THE USEFULNESS OF THE INVENTION

The usefulness or utility of this invention can be demonstrated by referring to the data presented in Tables 1, 2 and 3. All of the successful agents show that phellandrene can be separated from limonene by means of azeotropic distillation in a rectification column and that the ease of separation as measured by relative volatility is considerable.

WORKING EXAMPLE

1. Fifty grams of a phellandrene-limonene mixture and 50 grams ethanol were charged to a vapor-liquid equilibrium still and refluxed for two hours. Analysis indicated a vapor composition of 7.1% phellandrene, 92.9% limonene; a liquid composition of 4.5% phellandrene, 95.5% limonene. This is a relative volatility of 1.6.

I claim:

1. A method for recovering phellandrene from a mixture of phellandrene and limonene which consists essentially of distilling a mixture phellandrene and limonene in the presence of an azeotrope forming agent, recovering the phellandrene and the azeotrope forming agent as overhead product and obtaining the limonene as bottoms product, wherein said azeotrope forming agent consists of one material selected from the group consisting of 2-methoxyethanol, t-butyl methyl ether, ethyl formate, methyl propionate, ethyl lactate, ethanol, isopropanol, 1-propanol, 2-pentanol, 2-methyl-1-propanol, t-amyl alcohol, methanol, 1-methoxy-2-propanol, 1,4-dioxane, acetal, dioxolane, 4-hydroxy-4-methyl-2-pentanone, 2,2-dimethoxypropane, dimethylformamide, butyraldehyde, ethanolamine, acetonitrile, acetone, 2-butanone, 3-pentanone, cyclopentanone and n-butanol.

* * * * *